United States Patent [19]

Fisher

[11] Patent Number: 5,387,215
[45] Date of Patent: Feb. 7, 1995

[54] SURGICAL INSTRUMENT FOR CUTTING HARD TISSUE AND METHOD OF USE

[75] Inventor: Michael G. Fisher, Folsom, Calif.

[73] Assignee: Sierra Surgical Inc., Rancho Cordova, Calif.

[21] Appl. No.: 834,408

[22] Filed: Feb. 12, 1992

[51] Int. Cl.⁶ .............................................. A61B 17/00
[52] U.S. Cl. ....................................... 606/79; 606/85
[58] Field of Search ................... 606/79, 85, 84, 86, 606/87; 623/23

[56] References Cited

U.S. PATENT DOCUMENTS

| | | | |
|---|---|---|---|
| 505,818 | 10/1893 | Dallas | 606/85 |
| 2,740,406 | 4/1956 | Tofflemire | 606/79 |
| 3,395,709 | 8/1968 | Rubin | 606/85 |
| 4,124,026 | 11/1978 | Berner | 606/85 |
| 4,203,444 | 5/1980 | Bonnell et al. | |
| 4,589,414 | 5/1986 | Yoshida | 606/79 |
| 4,601,290 | 7/1986 | Effron et al. | |
| 4,625,725 | 12/1986 | Davison | 606/85 |
| 5,147,364 | 9/1992 | Comparetto | 606/85 |
| 5,169,402 | 12/1992 | Elloy | 606/85 |

OTHER PUBLICATIONS

Micro-Aire Product Catalog, released Oct. 1989.
Hall Surgical Product Catalog, release date unknown.

Primary Examiner—Michael A. Brown
Attorney, Agent, or Firm—Raymond B. Cranfill

[57] ABSTRACT

A surgical device capable of cutting and removing medium to hard body tissue such as cartilage and bone from a joint region or similarly restricted interior space within the body is disclosed. The surgical instrument includes a stationary carrier sized for insertion into a joint or similar restricted interior space within the body and having a first and second end. The carrier is provided with an apical aperture at the end to be inserted into the joint. A cutter is axially disposed within the carrier and is provided with at least one cutting surface at one end that protrudes from the aperture of the carrier. The cutter is further provided with an axial conduit that terminates in at least one opening on or proximate to the cutting surface of the cutter. The cutter is driven by a motor that moves the cutter in a linearly reciprocating fashion that abrades away tissue depending on the configuration of the cutting surface. The cutter is further provided with a vacuum source that is capable of creating suction at the opening of the axial conduit to draw tissue into the conduit opening and carry it away from the treatment site for disposal.

4 Claims, 3 Drawing Sheets

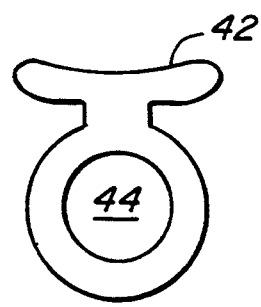
FIG. 4A.
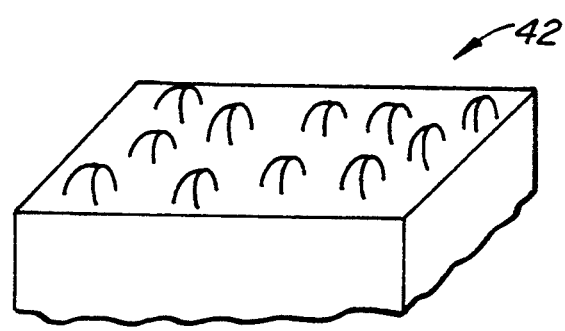
FIG. 5A.
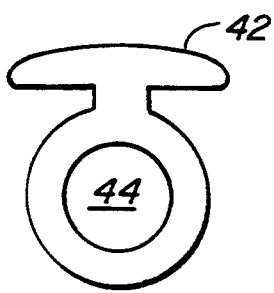
FIG. 4B.
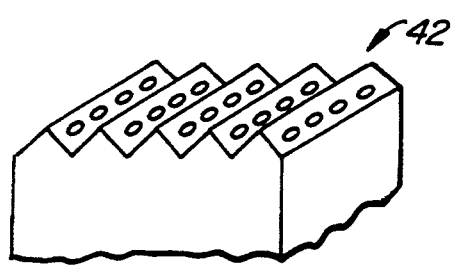
FIG. 5B.
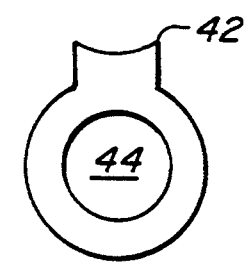
FIG. 4C.
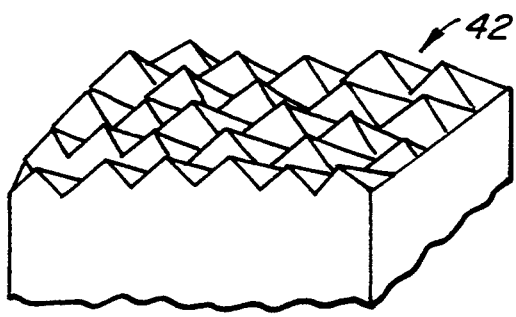
FIG. 5C.
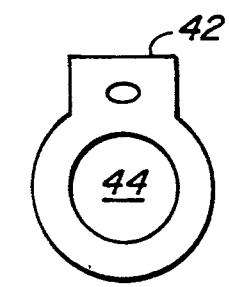
FIG. 4D.
FIG. 4E.

SURGICAL INSTRUMENT FOR CUTTING HARD TISSUE AND METHOD OF USE

FIELD OF THE INVENTION

This invention relates generally to surgical devices, and more particularly to surgical devices suitable for arthroscopic and laporoscopic applications.

BACKGROUND OF THE INVENTION

Over the last decade, minimally invasive surgical techniques have gained wide use and great popularity. Such techniques generally involve a combination of miniaturized cutting tools in concert with remote viewing devices that can be inserted through small incisions and delivered to a site well inside the body cavity to carry out desired surgery. Such techniques are advantageous over standard invasive surgery in that patient trauma is minimized and recovery time is markedly shortened.

One of the most popular applications of minimally invasive surgery is in the area of arthroscopic surgery. Such surgery allows joints to be repaired without having to cut through or open up healthy areas of the joint to be treated. However, operating within a joint is limited by the space available among and between the joint tissues and ligaments for maneuvering cutting devices.

In response to space limitations imposed on cutting devices to be used within joints and similarly constrained spaces, cutters relying on the shearing forces created by the interaction of at least two separate cutting surfaces have been proposed. U.S. Pat. No. 4,203,444 to Bonnell et al. discloses one such device. The Bonnell device utilizes an outer tube having a side-facing, axially extending cutting port and an internal rotary blade. A vacuum conduit draws the tissue to be sheared into the cutting port while the rotary blade is driven in shearing relation to the external tube. The vacuum further draws the cut body tissue through a tube lateral to the handle and out of a side port of the instrument for disposal.

U.S. Pat. No. 4,601,290 to Effron et al. discloses another example of a shearing cutter. The Effron device utilizes an outer tube having both a side-facing and end facing cutting port with a cutting edge and an internal tube having an internal opening having cutting edges thereon. The external and internal openings and edges are relatively moveable to open to receive the body tissue there through and to close in order to cut body tissue. A vacuum means into the external and internal openings where the tissue is sheared by the combined cutting forces of the internal and external tubes. The cut tissue is then drawn through the inner tube and subsequently out of the cutting device for disposal.

Unfortunately, existing cutting devices, such as those described above, exhibit serious problems that impair their usefulness in arthroscopic and other minimally invasive surgical applications. Some devices, such as the Bonnell instrument, are given to spooling or clogging when cutting through soft fibrous tissue. Further, rapid blade dulling, particularly when cutting very hard tissue such as cartilage or bone, often occurs significantly impairing the instrument's ability to cut hard tissues.

Another major disadvantage encountered with known surgical devices of this type stems from the cylindrical configuration of the rotating cutting edges. Much like the action of a mellon-bailer, tissue removal creates a depression with a curved, concave surface, as opposed to a box-like depression with more or less flattened sides. As much as the surgeon may attempt to match the equator of the concavity, removal of additional tissue always leaves behind a ridge or protrusion on the treated surface. Such protrusions are particularly disadvantageous in joint surgery where jagged or protruding surfaces on cartilage or bone can inhibit free joint movement and lead to pain and inflammation after surgery.

A further problem encountered is that of aspiration. Many existing cutting devices fail to aspirate the treatment area during surgery. Others employ a somewhat bulky and awkward side tube that is connected directly to the cutter rather than passing through the handle of the device.

In view of the foregoing, there is a need for a compact surgical cutting device for use in restricted spaces, the dimensions of which remain more or less constant during operation but that does not clog or spool during use and that effects prompt removal of tissue from the treatment site as the tissue is cut away by the cutting device. There is also a need for a surgical cutting device that leaves behind a surface that is more or less normal in topography for the joint or region being treated after desired tissue is removed, thereby avoiding the production of ridges, protuberances or odd shaping that may hinder or make painful joint movement after surgery. There is a further need for a surgical cutting device that permits more efficient cutting and sculpting of medium to hard body tissue in order to reduce the duration of surgery.

There is also a need for a surgical cutting device that allows soft tissue to be removed at selected times which at other times during an operation will act only on medium to hard tissue.

SUMMARY OF THE INVENTION

It is a general object of the invention to provide a compact surgical cutting device that is capable of creating a substantially normal surface after tissue removal.

Yet another object of the invention is to provide a method of removing tissue from a confined space, such as within a joint, that leaves behind a substantially normal joint surface capable of substantially normal joint function.

It is also a general object of the invention to provide a compact surgical cutting device that does not spool or otherwise become inoperable during surgery.

It is yet another object of the invention to provide a compact surgical cutting device in which the type and extent of cutting surface can be varied quickly by the surgeon during an operation.

Another object of the invention is to provide a compact surgical cutting device that is particularly suited to abrading through medium to hard tissues such as cartilage or bone.

Yet another object of the present invention is to provide a compact surgical cutting device suitable for laporoscopic and arthroscopic applications.

A further object of the present invention is to provide a compact surgical cutting device that is capable of removing tissue from a treatment site as the tissue is cut away.

The invention meets these objects by providing a surgical device capable of cutting and removing medium to hard body tissue such as cartilage and bone from a joint region or similarly restricted interior space within the body. The surgical instrument includes a stationary carrier sized for insertion into a joint or similar restricted interior space within the body and having a first and second end. The carrier is provided with an apical aperture at the end to be inserted into the joint. A cutter is axially disposed within the carrier and is provided with at least one cutting surface at one end that protrudes from the aperture of the carrier. The cutter is further provided with an axial conduit that terminates in at least one opening on or proximate to the cutting surface of the cutter. The cutter is driven by a motor that moves the cutter in a linearly reciprocating fashion that chops and/or abrades away tissue depending on the configuration of the cutting surface. Finally, the instrument is provided with a vacuum source that is capable of creating suction at the opening of the axial conduit. This suction draws cut tissue into the conduit opening and carries the tissue away from the treatment site through the length of the cutting device for disposal. The suction also assists in the cutting process by helping to maintain contact between the tissue and the cutting surface.

According to other aspects of the invention, the cutting surface of the cutter can be variously configured in order to obtain the desired sculptural effect. In one embodiment, a substantially planar surface with sharp projections is provided. Such a surface permits material to be abraded, as opposed to being sheared, thereby allowing the surgeon to leave behind a more or less planar surface after treatment. The cutter can also be configured to provide a blade forward of the abrasion surface. The combination of the blade and abrasion surface essentially permit the surgeon to use the surgical device much like a carpenter's plane. Other abrasion configurations, such as those with concave and convex surfaces, can also be provided for situations in which the surgeon wishes to leave behind a curved surface after tissue removal is completed.

The apparatus of the invention may also include a source of inert liquified gas, such as helium, argon or nitrogen connected to the axial conduit for delivery of liquified gas to the treatment site for hard freezing of soft tissues. Once hardened, such soft tissues may then be abraded away in the same fashion as cartilage and bone.

The invention also includes a method of removing tissue from restricted interior spaces of the body. According to the invention, a carrier or cutter is selected that has a diameter suitable for maneuvering within the space to be operated on. The instrument is then inserted into a joint through a small incision, or can be applied directly to the treatment site if the treatment site is already exposed, whereafter power is delivered to the motor to drive the cutter in a linearly reciprocating fashion. As pressure is applied by the surgeon, cartilage and/or bone is abraded away and then removed by suction through the central conduit to a waste disposal vessel.

The surgical device and method of the invention are advantageous over the prior art in that the cutting action of the device relies on abrasion and chopping to achieve tissue removal, not by a shearing force created by the action of cutting surfaces being brought together. Reliance on abrasion forces created by the linear reciprocation of a single cutting surface permits the surgeon to leave behind a more or less normal surface after the desired tissue is removed. Existing arthroscopic surgical devices leave behind curved surfaces and protruding ridges which can be highly disadvantageous to proper joint movement after the operation is complete.

Another distinct advantage of the invention is that it differentially acts upon harder tissues such as cartilage and bone without affecting the soft tissues of the joint. In operation, softer tissues flex away from the cutting surface. Because there is but one cutting surface, tissue cannot be caught and sheared as is the case with many known devices in which two cutting surfaces act in shearing cooperation.

A further significant advantage of the present invention is the capability for rapid reconfiguration of the cutting surface. Existing arthroscopic surgical devices are characterized by fixed blade configurations, largely because they rely upon the shearing interactions between two separate blade systems. Because the blade configuration cannot be easily changed, the ability to create a desired topography on the treatment surface is also limited when using known arthroscopic surgical devices.

The invention is also advantageous in that it allows the selected removal of soft tissues in addition to medium to hard tissues by hard freezing soft tissue with an inert liquid gas. Because the cutting operation of the invention will not affect soft tissues that have not been hardened by freezing, the present invention allows such tissues to be differentially removed. Existing cutting devices affect soft, medium and hard tissues similarly and do not allow for the differential removal of soft tissues relative to such harder tissues as bone and cartilage.

These and other objects and advantages of the invention will become more fully apparent when the following detailed description of the invention is read in conjunction with the accompanying drawings.

BRIEF DESCRIPTION OF THE DRAWINGS

FIGS. 4A–E are views in cross section of the cutter of the surgical device of the invention.

FIGS. 5A–C are perspective views of the cutting surface of the cutter of the surgical device of the invention.

DETAILED DESCRIPTION OF THE INVENTION

Figure 1:
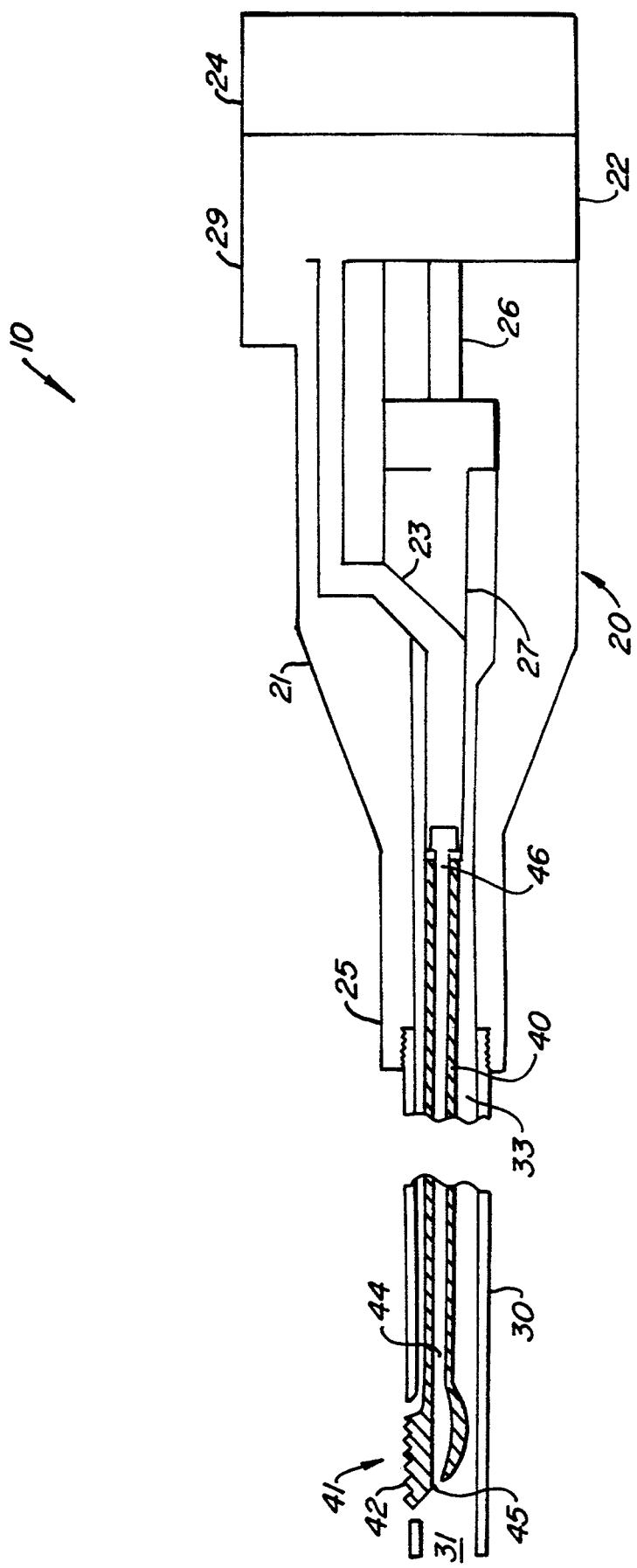
FIG. 1 is a view in cross-section of an embodiment of the surgical device of the invention.
Figure 2:
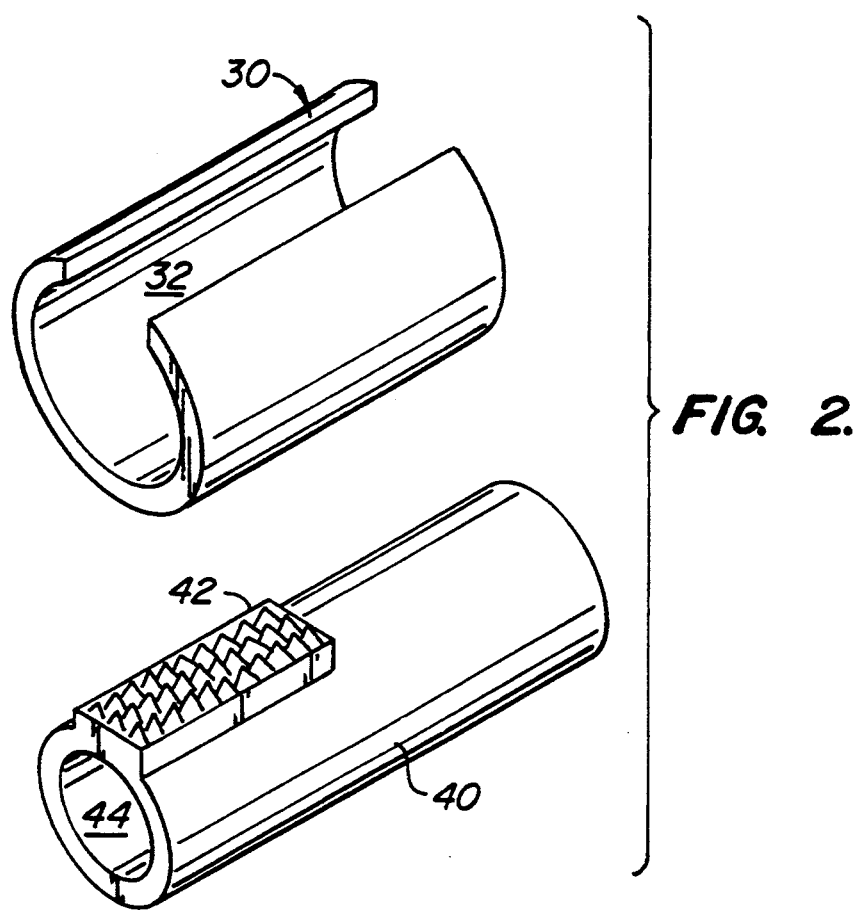
FIG. 2 is a perspective view of the cutter and carrier of the surgical device of the invention.

Turning now to FIG. 1, the surgical device of the invention will now be described. For the purposes of the following disclosure, the end of the device that is closest to or in contact with the patient is designated the distal end. The end closest to the surgeon is designated the proximal end.

The surgical device 10 includes a drive handle 20, a carrier means 30, such as a cannula, and a cutter 40. Drive handles, such as drive handle 20, are well known components of arthroscopic surgical instruments, and generally include a housing 2, a motor 22, a carrier mount 25 fixed in stationary relation to housing 21, and drive shaft 26 connected to motor 22, and a cutter mount 27 connected to drive shaft 26 as shown in FIG. 1. Examples of typical drive handles include reciprocators produced by Micro-Aire (model no. 1400) and Hall (model nos. micro 100 and Micro E). The drive handle of the present invention differs from existing devices in that it is provided with an internal aspiration channel 23 connected to a vacuum source permitting the cutter 40 to function both as a cutter and as an aspirating device. Additionally, the drive handle can fitted with a source of liquidified inert gas 29 such as argon, helium or nitrogen. Gas source 29 is coupled at a desired point with aspiration channel 23. In this way, liquified inert gas can be delivered to the operation site through the aspiration channel in order to freeze, and thus harden, softer tissues that otherwise could not be abraded and removed by the cutter of the invention.

Figure 3:
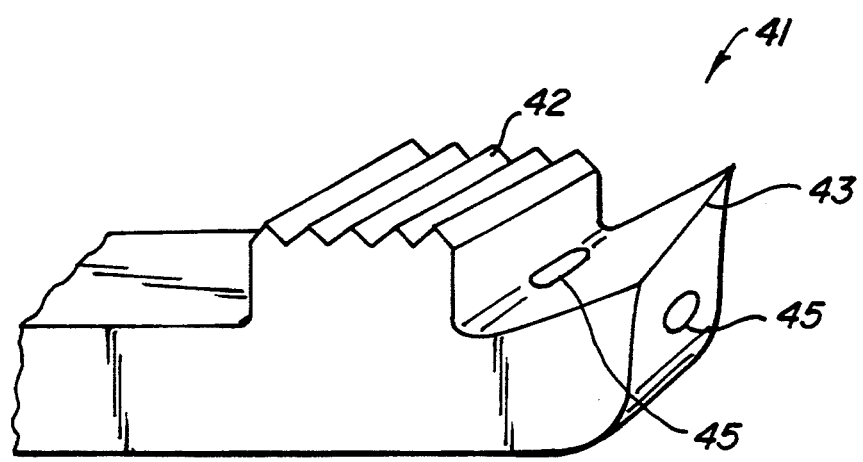
FIG. 3 is a perspective view of an embodiment of the cutter of the surgical device of the invention.

Cutter 40 comprises a rod that at its proximal end can be fixedly connected to drive shaft 26 of drive handle 20. At its distal end, cutter 40 is provided with a cutting surface 41. Cutting surface 41 can be variously configured to achieve different cutting styles and surface sculpturing. In the another embodiment, cutting surface 41 is provided with a rasping pad 42 and a blade 43, as shown in FIG. 3. Rasping pad 42 is preferably substantially planar, but may be varied in shape in order to achieve specific sculpturing results. FIGS. 4A–E show the distal end of the cutter in cross-section, showing the different surface curvatures that are possible with the rasping pad. Such variation in surface curvature may be desireable where a surgeon wishes to produce other than a flat surface at the treatment site.

The surface of rasping pad 42 can also be varied to achieve different abrasive effects. One possible rasping surface is comprised of a plurality of sharp-pointed, more or less cone-shaped projections, as shown in FIG. 3. Other surface projections may also be suitable, such a series of substantially parallel sharp-edged ridges, interlocking pyramidally-shaped teeth or semicircular sharp-edged projections, all as shown in FIG. 5. The specific configuration chosen will depend on the type and amount of tissue to be abraded.

In addition to rasping pad 42, cutter 40 is preferably provided with a blade 43 positioned forward of the rasping pad. The blade allows the surgeon to chop or shave off, as opposed to abrade, larger pieces of tissue than could be removed by the rasping pad alone. As described in greater detail below, both the blade 43 and the rasping pad 42 operate together during the cutting procedure much like a carpenter's plane, removing pieces of tissue and then smoothing over the surface to achieve a substantially planar surface after treatment.

Cutter 40 is further provided with a central channel or conduit 44 that terminates at the distal end of the cutter in an opening 45 on or proximate to rasping pad 42 and at the proximal end in an opening 46 that is coupled in a fluid-tight configuration with the aspiration conduit of drive handle 20. Central conduit 44 provides a path through which cut away tissue and fluid exudate can be removed, thereby providing the surgeon with a better view of the treatment area during the operation.

Cutter 40 can be made out of any suitable material that is both strong and resistent to shocks and stresses encountered in surgery. It is preferred that the cutter be able to operate at reciprocations of up to 200,000 cycles per minute. Further, the composition of the material should not contain biotoxic elements or compounds. In this regard, the chrome content of the composition should be less than 10%. The composition must also have a Knoop hardness of 466 or greater in order to ensure continued cutting efficiency. A number of compositions meet or exceed these specifications including ceramics such as Alumina, Zirconia, MgO partially stabilized TTZ, and tempered titanium. It is also preferable to utilize materials that can be injection molded. Injection molding obviates the need to drill aspiration channels in the cutter, thereby significantly reducing both production time and production cost. Both tempered titanium and zirconia ceramics are preferable in this regard.

Cannula 30 is a hollow tube sized to receive a desired diameter of cutter 40. Cannula 30 is provided with an opening 31 and a channel 32 at its distal end and with an opening 33 at its proximal end. As will be appreciated from the figures, cutter 40 is inserted distally through opening 31 of the cannula and then connected to the drive shaft of the motor in drive handle 20. The diameter of cutting surface 41 of cutter 40 is configured to be slightly less than that of the lateral channel 32 of the cannula. In this way, the channel can act as a track or guide for the cutting surface as the cutter moves up and down within the cannula.

It will be appreciated that the cannula in no way participates in or contributes to the cutting action of surgical device of the invention. Rather, the purpose of the cannula is generally as a guide in inserting the cutter into an interior space, such as a joint, and to act as a guide for and thus stabilize somewhat the linearly reciprocating motion of the cutting block of the cutter. In particularly inaccessible joint surfaces, such as those in the shoulder, the cannula preserves the access path of the cutter into the joint so that the cutter may be removed, replaced and reinserted without having to rediscover the original access channel or create a new one. Manufacture of the cannula is preferred to be of a radio lucent material such as titanium or radio lucent plastic.

It will be appreciated that the operation of the cutting device of the present invention differs considerably from that of known prior art devices. Because the cutter of the invention utilizes abrasion forces, a surgeon can much more easily remove irregularly shaped deposits and protuberances than is possible with shearing cutters generally now used. When abrasion force is applied to such a deposit, it is possible to erode away from the apex of the protuberance to the base in a controlled fashion. Shearing devices and rotating abrading devices, such as burs, are suited to more planar surfaces. When applied to areas of the joint with strong curvature, they tend to jump or skip over the surface without achieving much satisfactory cutting.

The operation of the invention also permits more versatility in surface sculpturing. Unlike conventional abrading apparatus, such as rotating burs that leave behind sharp ridges and valleys, the cutter of the present invention can be used to shape surfaces more precisely, whether they be flat or curved. This sculpturing capacity is particularly important in the field of joint repair and reconstruction where the finished joint surface is critical to operation and well being of the repaired joint. Irregular surfaces frequently left behind by conventional devices often result in inflammation, pain, loss of mobility and recurrence of pathology that the operation was originally intended to cure.

From the foregoing, it will be appreciated how the objects and features of the invention are met. The surgical cutting device of the invention permits the differential removal of medium to hard body tissues such as cartilage and bone without cutting or abrading the softer surrounding tissues. The invention also provides a means of removing surgical detritus and exudate from the operating site through the cutter and the drive handle, thereby improving operation efficiency by maintaining a more or less debris-free operation site and by increasing maneuverability of the drive handle. Perhaps most importantly, the cutting device of the invention permits a surgeon to remove unwanted deposits or tissue from the joint while at the same time retain a substantially normal joint surface that can operate and function normally once the joint is reassembled. Further, the abrasion force applied by the cutter of the invention allows a surgeon to remove protuberances, such as calcareous deposits, and similar irregularly shaped deposits in a more controlled fashion than is possible using prior art devices.

Although the invention has been described with respect to a particular apparatus and method for arthroscopic or laporoscopic surgery, it will be appreciated that various modifications of the apparatus and method are possible without departing from the invention, which is defined by the claims set forth below.

I claim:

1. A surgical instrument for cutting and removing medium to hard body tissue such as cartilage and bone from a joint region or similar restricted interior space within a body, said instrument comprising:
   a) cutting means having a first end and a second end, said cutting means provided at the first end with a cutter comprising a blade terminally positioned and a rasping pad rearward of the blade, said cutting means further provided with an axial conduit terminating in a plurality of openings on or proximate to the cutter;
   b) drive means connected to the second end of said cutting means, said drive means operative to move the cutter in a linearly reciprocating fashion to cut away pieces of tissue; and
   c) vacuum means operative to produce a suction force at the openings of the axial conduit of said cutting means for removing cut away tissue pieces from the interior space.

2. A surgical instrument for cutting and removing medium to hard body tissue such as cartilage and bone from a joint region or similar restricted interior space within a body, said instrument comprising:
   a) stationary carrier means sized for insertion into a joint or similar restricted interior space within the body, said stationary carrier means having a first end and a second end, provided lengthwise with an axial channel, and terminating at the first end in an aperture;
   b) cutting means axially disposed within said carrier means, said cutting means having a first end and a second end and provided at the first end with a cutter comprising a terminally positioned blade and a rasping pad positioned rearward of the blade, said cutting means further provided with an axial conduit terminating in a plurality of openings on or proximate to the cutter;
   c) drive means connected to the second end of said cutting means, said drive means operative to move the cutter and rasping pad in a linearly reciprocating fashion to cut away pieces of tissue; and
   d) vacuum means operative to produce a suction force at the openings of the axial conduit of said cutting means for removing cut away tissue pieces from the interior space.

3. A surgical instrument for cutting and removing medium to hard body tissue such as cartilage and bone from a joint region or similar restricted interior space within a body, said instrument comprising:
   a) stationary carrier means sized for insertion into a joint or similar restricted interior space within the body, said stationary carrier means having a first end and a second end, provided lengthwise with an axial channel, and terminating at the first end in an aperture;
   b) cutting means axially disposed within said carrier means, said cutting means having a first end and a second end and provided at the first end with a cutter comprising a terminally positioned blade and a substantially planar rasping pad positioned rearward of the blade, said cutting means further provided with an axial conduit terminating in a plurality of openings on or proximate to the cutter;
   c) drive means connected to the second end of said cutting means, said drive means operative to move the cutter and rasping pad in a linearly reciprocating fashion to cut away pieces of tissue; and
   d) vacuum means operative to produce a suction force at the openings of the axial conduit of said cutting means for removing cut away tissue pieces from the interior space,
wherein the channel of said stationary cutting means forms a track which guides the linearly reciprocating movement of the cutting means.

4. A surgical instrument for cutting and removing medium to hard body tissue such as cartilage and bone from a joint region or similar restricted interior space within a body, said instrument comprising:
   a) cutting means having a first end and a second end, said cutting means provided at the first end with a cutter comprising a terminally positioned blade and a rasping pad positioned rearward of the blade, said cutting means further provided with an axial conduit terminating in a plurality of openings on or proximate to the cutter;
   b) drive means connected to the second end of said cutting means, said drive means operative to move the rasping pad and cutter in a linearly reciprocating fashion to cut away pieces of tissue;
   c) freezing means for delivering a liquified inert gas to the operation site to harden soft tissue for cutting; and
   d) vacuum means operative to produce a suction force at the openings of the axial conduit of said cutting means for removing cut away tissue pieces from the interior space.

* * * * *